(12) United States Patent
Ogata et al.

(10) Patent No.: US 6,310,067 B1
(45) Date of Patent: Oct. 30, 2001

(54) UROCANIC ACID DERIVATIVES

(75) Inventors: Kazumi Ogata, Toyonaka; Kazuhiko Ito, Amagasaki; Takahiro Sakaue, Itami; Sachiko Inoue, Akashi; Shinya Ogino, Itami, all of (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/601,532

(22) PCT Filed: Feb. 3, 1999

(86) PCT No.: PCT/JP99/00469

§ 371 Date: Aug. 3, 2000

§ 102(e) Date: Aug. 3, 2000

(87) PCT Pub. No.: WO99/40071

PCT Pub. Date: Aug. 12, 1999

(30) Foreign Application Priority Data

Feb. 5, 1998 (JP) .................................................. 10-024623

(51) Int. Cl.$^7$ .......................... A61K 31/50; A01N 43/58; C07D 239/72; C07D 277/04; C07D 409/00
(52) U.S. Cl. .................. 514/253.09; 514/253.01; 514/254.05; 514/259; 514/370; 514/397; 514/399; 514/400; 544/284; 544/286; 544/360; 544/370; 548/190; 548/312.1; 548/314.7; 548/335.1; 548/335.5; 548/336.1; 548/341.5; 549/59; 549/65; 549/66; 549/68
(58) Field of Search .................. 514/253.01, 253.09, 514/254.05, 259, 370, 397, 399, 400; 544/284, 286, 360, 370; 548/312.1, 314.7, 335.1, 335.5, 190, 341.5, 336.1; 549/59, 65, 66, 68

(56) References Cited

FOREIGN PATENT DOCUMENTS

| 56-161314 A | 12/1981 | (JP) . |
| 60-16907 A | 1/1985 | (JP) . |
| 97/39748 | * 10/1997 | (WO) . |
| WO 97/39748 | 10/1997 | (WO) . |

* cited by examiner

Primary Examiner—Mukund J. Shah
Assistant Examiner—Tamthom N. Truong

(74) Attorney, Agent, or Firm—Armstrong, Western, Hattori, McLeland & Naughton, LLP

(57) ABSTRACT

Urocanic acid derivatives useful as antiallergic agents represented by the following formula (I) or a pharmacologically acceptable salt thereof:

wherein $R_2$ denotes hydrogen or lower alkyl, $R_3$ denotes nitro, amino, cyano or $COOR_2$,
wherein $R_2$ in said $COOR_2$ is as defined above, and Q denotes carbon or nitrogen.

9 Claims, 2 Drawing Sheets

UROCANIC ACID DERIVATIVES

TECHNICAL FIELD

The present invention relates to novel urocanic acid derivatives, a method of preparation thereof, and antiallergic medicaments containing thereof.

BACKGROUND ART

Urocanic acid, first discovered in dog urine in 1874 by Jaffe and later confirmed to occur also in human urine and epidermis, is a compound of the following formula (II).

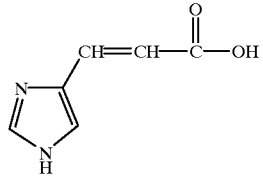

(II)

Urocanic acid is thought to act as an ultraviolet absorbent and thus serve to protect the slin. Urocanic acid is also reported to have a suppressive effect on delayed allergy [The Allergy In Practice, 15(9):1995]. In addition, urocanic acid bound by ascorbic acid (Japanese Laid-Open Patent Application No. S56-161314) and thiol urocanic acid (Japanese Laid-Open Patent Application No. S60-16907) are known to have a skin brightening effect.

With its antiallergic effect, however, urocanic acid has its own shortcomings that it is only poorly soluble in water and organic solvents, thereby maling itself hard to be formulated into pharmaceutical preparations, and that its suppressive effect on delayed allergy is by no means satisfactory.

Upon the above background, the present inventors investigated to obtain urocanic acid derivatives that have sufficient solubility in water or organic solvents and having potent antiallergic effects. As a result, certain urocanic acid derivatives were found to have potent antiallergic effects and, at the same time, sufficient solubility in water or organic solvents. The present inventors completed the present invention through further investigation based on this finding.

The present invention provides urocanic acid derivatives having sufficient solubility in water or organic solvents and having potent antiallergic effects.

DISCLOSURE OF INVENTION

Thus, the present invention relates to (1) a urocanic acid derivative represented by the following formula (I) or a phannacologically acceptable salt thereof (hereinafter referred to as the "present compound"):

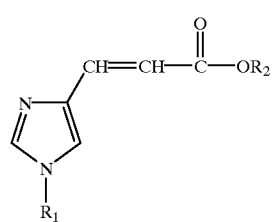

(I)

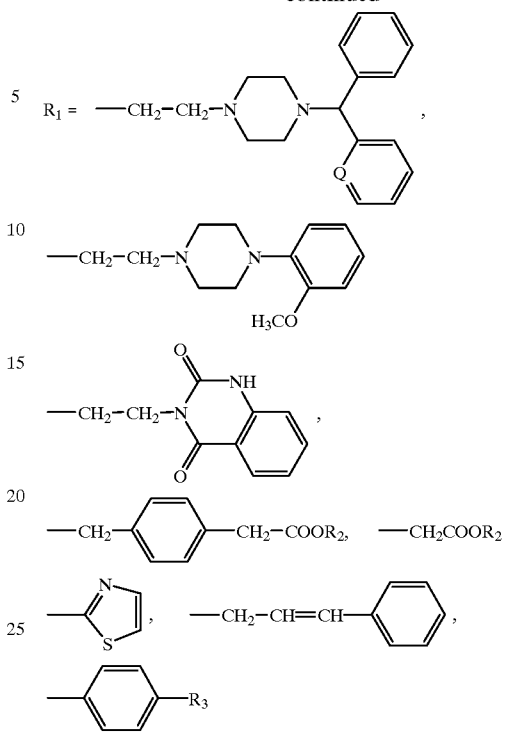

wherein $R_2$ denotes hydrogen or lower alkyl, $R_3$ denotes nitro, amino, cyano or $COOR_2$,
wherein $R_2$ included in said $COOR_2$ is as defined above, and Q denotes carbon or nitrogen,
(2) a method for preparation thereof, and
(3) an antiallergic medicament comprised thereof.

Examples of the present compound include the following specific compounds and their pharmacologically acceptable salts.

(1) 1-(diphenylmethylpiperazinylethyl)urocanic acid methyl ester
(2) 1- (diphenylmethylpiperazinylethyl)urocanic acid
(3) 1-[phenyl(2-pyridyl)methylpiperazinylethyl]urocanic acid methyl ester
(4) 1-(4-nitrophenyl)urocanic acid methyl ester
(5) 1-(4-aminophenyl)urocanic acid methyl ester
(6) 1-(diphenylmethylpiperaiinylethyl)urocanic acid ethyl ester
(7) 1-(4-cyanophenyl)urocanic acid methyl ester
(8) 1-(4-cyanophenyl)urocanic acid
(9) 1-(2,5-thiazolyl)urocanic acid methyl ester
(10) 1-(4-carboethoxyphenyl)urocanic acid methyl ester
(11) 1-(4-carboxyphenyl)urocanic acid
(12) 1-(4-carboethoxyphenyl)urocanic acid ethyl ester
(13) 1-((4-carbomethoxymethylphenyl)methyl)urocanic acid methyl ester
(14) 1-((2-methoxyphenyl)piperazinylethyl)urocanic acid ethyl ester
(15) 1-(2-(2,4-dioxo-1,3-dihydroquinazoline-3-yl)ethyl)urocanic acid ethyl ester
(16) 1-(carboethoxymethyl)urocanic acid ethyl ester
(17) 1-(3-phenyl-2-propenyl)urocanic acid methyl ester

BEST MODE FOR CARRYING OUT THE INVENTION

Figure 1:
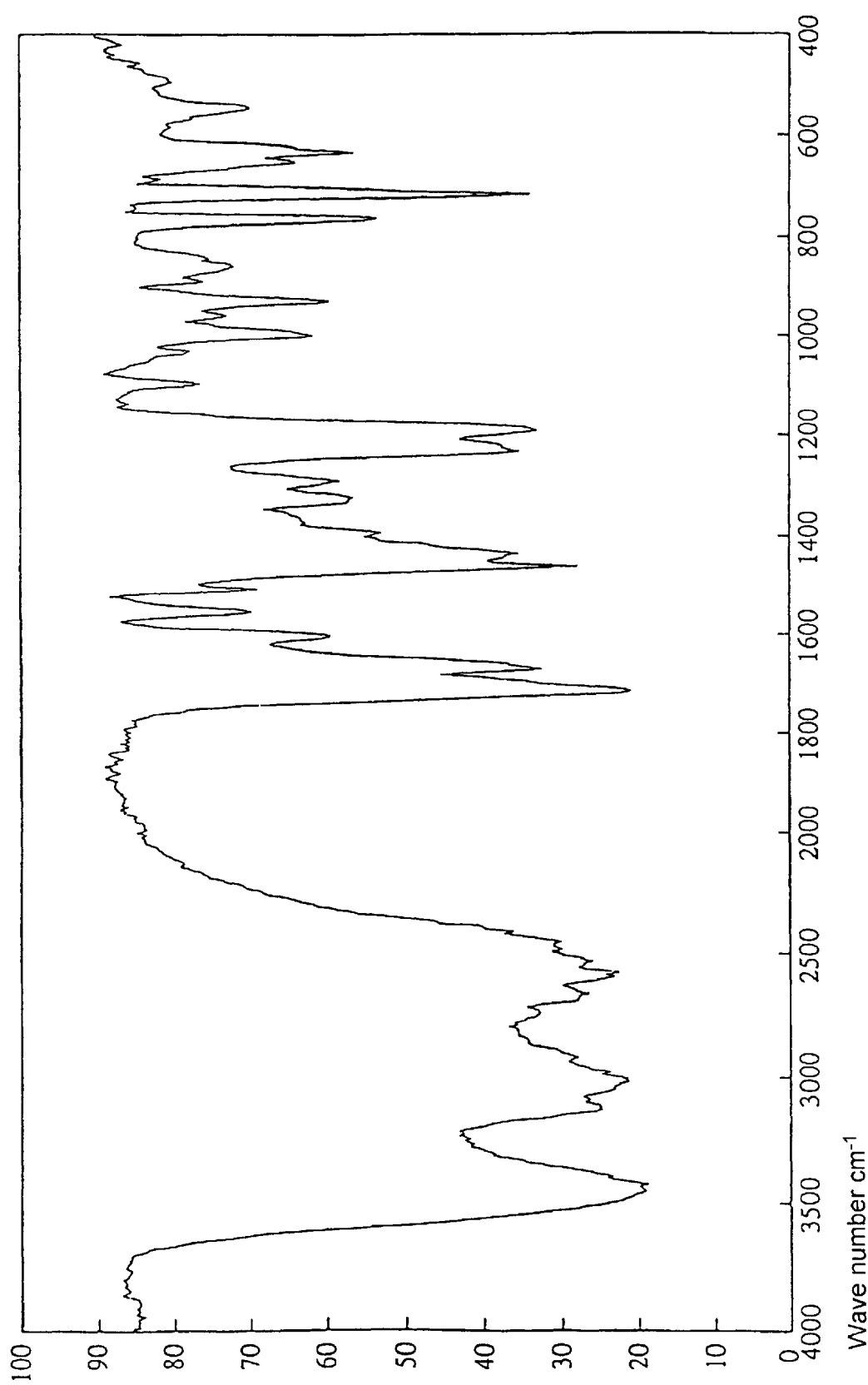
FIG. 1 illustrates infrared (IR) absorption spectrum of the compound synthesized in Example 2.
Figure 2:
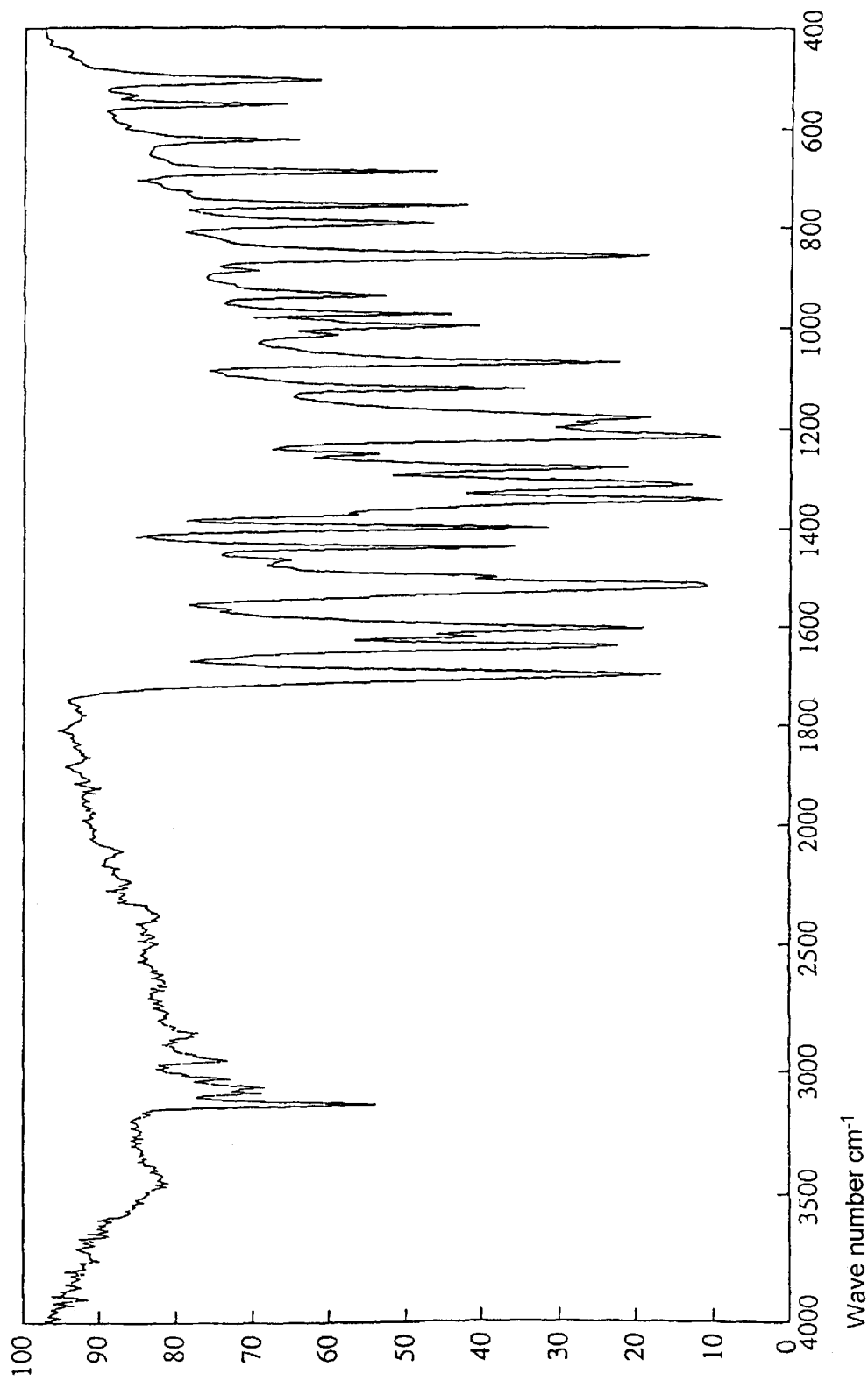
FIG. 2 illustrates infrared (IR) absorption spectrum of the compound synthesized in Example 5.

The lower alkyl for $R_2$ in the above formula (I) is preferably C1 to C5 linear, branched or cyclic alkyl, which may be, for example, methyl, ethyl, n-propyl, isopropyl, cyclopropyl, n-butyl, tert-butyl, sec-butyl, n-pentyl, 1-ethylpropyl, and isopentyl.

The nitro or amino for $R_3$ in the formula may be substituted. Substitution groups may be lower alkyl (the lower alkyl as defined for $R_2$), for example.

The present compound represented by the above formula (I) may be used for the purpose of the present invention either in its free acid form or in the form of pharmacologically acceptable salt thereof. Examples of its pharmacologically acceptable salt include alkaline metal salts such as sodium salts and potassium salts, as well as alkaline earth metal salts such as calcium salts and magnesium salts. Also included are inorganic acid salts such as hydrochlorides, sulfates and nitrates, as well as organic acid salts such as maleates and tartrates. Any other salts may be used insofar as they are pharmacologically acceptable.

The present compound can be synthesized according to the following scheme of synthesis or analogously thereto.

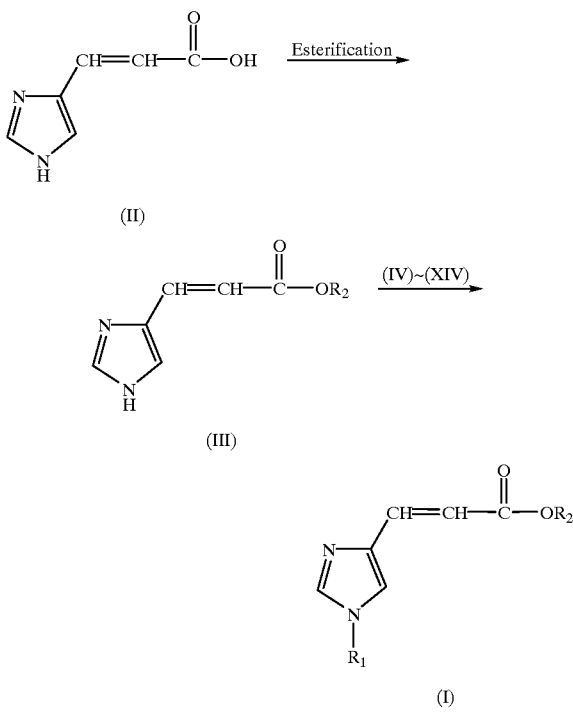

[In the scheme, $R_1$ and $R_2$ are as defined hereinbefore.]

The present compound represented by the formula (I) can be obtained by reacting urocanic acid ester (III) obtained by esterification of urocanic acid (II) with a halogenated compound (IV)–(XIV) (wherein the halogen is fluorine, chlorine, iodine, or bromine), or further by hydrolyzing the reaction product.

One of the raw material, urocanic acid ester (III), can be obtained by heating urocanic acid (II) in an alcohol, e.g. methanol or ethanol, in the presence of sulfuric acid in a conventional manner.

Another raw material, a halogenated compound such as diphenylmethyl-piperazinylethyl chloride (IV), phenyl(2-pyridyl)methylpiperaziylethyl chloride (V), (2-methoxyphenyl)piperazinylethyl chloride (VI), 3-(2-chloroethyl)-2,4(1H, 3H)-quinazolinedione (VII), fluorobenzonitrile (VIII), fluorobenzoic acid alkyl ester (IX), fluoronitrobenzene (X), bromothiazole (XI), bromomethylphenylacetic acid (XII) alkyl ester, 3-phenyl-2-propene chloride (XIII) or bromoacetic acid (XIV) alkyl ester, may be those commercially available (the alkyl for the alkyl esters are as defined hereinbefore for $R_2$).

The urocanic acid ester (III) obtained above is dissolved in dimetht formaldehyde and cooled while stirring. To this is added sodium hydride, and the mixture is brought back to room temperature and stirred for 10–60 min. Then, one of the raw material halogenated compounds (IV)–(XIV) is added and heated to about 50–150° C. and reaction is allowed for about 1–24 hrs. After evaporation of the solvent, recrystallization from a proper solvent such as an alcohol, ether or ethyl acetate gives a corresponding one of the present compound (I) in an ester form (in the formula, $R_2$ =lower alkyl). A corresponding free acid form (in the formula, $R_2$ =hydrogen) of the present compound (I) can be obtained through hydrolysis of the ester in the presence of sodium hydroxide in an alcohol and then recrystallization from a suitable solvent such as water, alcohol or acetic acid.

The present compound (I) thus obtained may be provided in the from of a pharmacologically acceptable salt as described above using a known method.

The present compound (I) obtainable as above is a novel compound that has not so far been found in publications, and it is useful as an antiallergic medicament.

The antiallergic medicament of the present invention is particularly useful against type I as well as delayed allergies. Examples of specific allergic diseases that can be treated with the antiallergic medicament of the present invention include bronchial asthma, pollinosis, allergic rhinitis, alimentary allergic gastritis, allergic diarrhea, ulcerative colitis, stomatitis, nodular periarteritis, obliterating endarteritis, endocarditis, urticaria, eczema, contact-type dermatitis, phlyctenosis, sympathetic ophthalmia, allergic conjunctivitis and allergic keratitis.

The medicament of the present invention may contain one or more species of the present compound (I) in combination, according to the purpose and needs.

The medicament of the present invention is used as an antiallergic medicament, either orally or parenterally. It may be made into any preparation forms such as solid preparations including tablets, granules, powders and capsules or liquid preparations including injections and eye drops, using any of known methods. Such preparations may contain conventional additives such as excipients, binders, thickeners, dispersing agents, resorption enhancers, buffering agents, surfactants, solubilizing agents, preservatives, emulsifiers, isotonizers, stabilizers, and pH adjusting agents.

The dose of the present compound when used as an antiallergic agent may be: e.g., about 1 mg to about 30 mg once a day for adults, in the case of injection, and about 1 mg to about 100 mg at a time, which is repeated several time a day, for adults, in the case of oral preparations, although the dose may vary in accordance with the employed species of the present compound, the body weight or age of the patient, the given disease to be treated and its condition, and the route of administration. In the case of eye drops, a preparation preferably of a concentration of about 0.01 to 5 (w/v) % is applied several times a day, by a few drops at a time, for adults.

The medicament of the present invention may further contain other antiallergic agents and/or components having other pharmacological activities insofar as they do not contradict the purpose of the present invention.

BEST MODE FOR CARRYING OUT THE INVENTION

The present invention is described in further detail below with reference to examples.

EXAMPLE 1

1-(Diphenylmethylpiperazinylethyl)urocanic Acid Methyl Ester

A mixture of 0.6 g of sodium hydride (60% content) suspended in 30 ml of dimethylformamide (DMF) was slowly added dropwise to a solution of 1.9 g of urocanic acid methyl ester dissolved in 20 ml of DMF, while ice-cooling. After completion of the addition, the mixture was brought back to room temperature and then heated to 60° C. for 1 hr. After cooling to room temperature, a solution of 4.0 g of 1-diphenylmethyl-4-(2-chloroethyl)piperazine dissolved in 20 ml of DMF was added and the mixture stirred for 12 hrs at 100° C. To the reaction mixture was added water and precipitated crystals were collected by filtration. Recrystallization of the thus obtained crystals from ethyl acetate gave 2.3 g of white crystals, m.p. 175° C.–176° C.

Elemental analyses: for $C_{26}H_{30}N_4O_2$; Calculated (%): C, 72.53; H, 7.02; N, 13.01 ; Found (%): C, 72.29; H, 7.05; N, 12.75.

EXAMPLE 2

1-(Diphenylmethylpiperazinylethyl)urocanic Acid 1.0 g of 1-(diphenylmethylpiperazinylethyl)urocanic acid methyl ester obtained in Example 1 was subjected to hydrolysis in a solution made of 30 ml of methanol and 30 ml of 0.5 N sodium hydroxide, and, after neutralization with acetic acid, extracted with chloroform. After evaporation of the solvent and conversion of the residue to hydrochloric acid salt by addition of 2N hydrochloric acid, recrystaized from methanol-acetone gave 0.8 g of white crystals, m.p. 202° C.–205° C. (decomp.).

Elemental analyses: for $C_{25}HN_4O_2 \cdot 4HCl \cdot 1.5H_2O$; Calculated (%): C, 50.95; H, 5.99; N, 9.51; Found (%): C, 50.91; H, 5.98; N, 9.23.

EXAMPLE 3

1-[Phenyl(2-pyridyl)methylpiperazinylethyl] urocanic Acid Methyl Ester

Reaction and workup were carried out as in Example 1 using 0.8 g of urocanic acid methyl ester, 0.3 g of sodium hydride, 1.7 g of 1-[phenyl (2-pyridyl)methyl]-4-(2-chloroethyl)piperazine. Recrystallization from ethyl acetate-isopropyl ether gave 0.9 g of white crystals, m.p. 167–169° C.

Elemental analyses: for $C_{25}H_{29}N_5O_2 \cdot 0.25H_2O$; Calculated (%): C, 68.86; H, 6.82; N, 16.06; Found (%): C, 68.67; H, 6.69; N, 15.88.

EXAMPLE 4

1-(4-Nitrophenyl)urocanic Acid Methyl Ester

Reaction and workup was carried out as in Example 1 using 3.0 g of urocanic acid methyl ester and 5.6 g of p-nitrofluorobenzene, giving yellow solid. Its recrystallization from DMF gave 4.0 g of pale yellow crystals, m.p. 255–256° C.

Elemental analyses: for $C_{13}H_{11}N_3O_4$; Calculated (%): C, 57.14; H, 4.06; N, 15.38; Found (%): C, 57.20; H, 4.12; N, 15.57.

EXAMPLE 5

1-(4-Aminophenyl)urocanic Acid Methyl Ester 1.0 g of the compound of Example 4 was dissolved in 20 ml of acetic acid. 1.9 g of stannous chloride was added and the mixture was refluxed for 10 min with heating. The solvent was evaporated under reduced pressure and the residue was neutralized with 2N sodium hydroxide and extracted with chloroform. After evaporation of the solvent, the residue thus obtained was purified by silica gel chromatography (ethyl acetate:hexane=4:1). Recrystallization from ethyl acetate-ether gave 0.5 g of yellow crystals, m.p. 154–156° C.

Elemental analyses: for $C_{13}H_{15}N_3O_2 \cdot 0.25H_2O$; Calculated (%): C, 63.02; H, 5.49; N, 16.96; Found (%): C, 63.06; H, 5.41; N, 17.04.

EXAMPLE 6

1-(Diphenylmethylpiperazinylethyl)urocanic Acid Ethyl Ester

Reaction and workup were carried out as in Example 1 using 1.7 g of urocanic acid ethyl ester and 3.8 g of 1-diphenyl-4-(2-chloroethyl)piperazine. Recrystallization of thus obtained crystals from ethanol-isopropyl ether gave 2.4 g of white crystals, m.p. 140–142° C.

Elemental analyses: for $C_{27}H_{32}N_4O_2 \cdot 0.25H_2O$; Calculated (%): C, 72.21; H, 7.29; N, 12.48; Found (%): C, 72.17; H, 7.21; N, 12.31.

EXAMPLE 7

1-(4-Cyanophenyl)urocanic Acid Methyl Ester

Reaction and workup were carried out as in Example 1 using 3.0 g of urocanic acid methyl ester and 3.6 g of 4-fluorobenzonitrile. Recrystallization of thus obtained crystals from methanol gave 3.0 g of white crystals, m.p. 248–250° C. (decomp.).

Elemental analyses: for $C_{14}H_{11}N_3O_2 \cdot 0.25H_2O$; Calculated (%0): C, 65.24; H, 4.49; N, 16.30; Found (%): C, 64.87; H, 4.21; N, 16.23.

EXAMPLE 8

1-(4-Cyanophenyl)urocanic Acid 1.5 g of the compound obtained in Example 7 was subjected to hydrolysis as in Example 2. Recrystallization of thus obtained crystals from acetic acid gave 0.5 g of white crystals, m.p. 283–285° C. (decomp.).

Elemental analyses: for $C_{13}H_9N_3O_2 \cdot 0.25H_2O$; Calculated (%): C, 64.06; H, 3.93; N, 17.24; Found (%): C,63.81; H, 4.01; N, 17.33.

EXAMPLE 9

1-(2,5-Thiazolyl)urocanic Acid Methyl Ester

Reaction and workup were carried out as in Example 1 using 3.0 g of urocanic acid methyl ester and 4.9 g of 2-bromothiazole. Recrystallization of thus obtained crystals from ethyl acetate-isopropyl ether gave 1.4 g of pale brown crystals, m.p. 154–155° C.

Elemental analyses: for $C_{10}H_9N_3O_2S$; Calculated (%): C, 51.05; H, 3.85; N, 17.86; Found (%): C, 51.44; H, 4.03; N, 18.25.

EXAMPLE 10

1-(4-Carboethoxyphenyl)urocanic Acid Methyl Ester

Reaction and workup were carried out as in Example 1 using 3.0 g of urocanic acid methyl ester and 5.1 g of 4-fluorobenzoic acid ethyl ester. Recrystallization of thus obtained crystals from methanol gave 3.3 g of white crystals, m.p. 180–184° C. (decomp.).

Elemental analyses: for $C_{16}H_{16}N_2O_4 \cdot 0.25H_2O$; Calculated (%): C, 63.05; H, 5.45; N, 9.19; Found (%): C, 63.19; H, 5.21; N, 9.22.

EXAMPLE 11

1-(4-Carboxyphenyl)urocanic Acid 1.5 g of the compound of Example 10 was subjected to hydrolysis as in Example 2. Recrystallization of thus obtained crystals from water gave 1.3 g of white crystals, m.p. over 300° C. (decomp.).

Elemental analyses: for $C_{13}H_{10}N_2O_4$; Calculated (%): C, 60.47; H, 3.90; N, 10.85; Found (%): C, 60.23; H, 3.98; N, 10.96.

EXAMPLE 12

1-(4-Carboethoxyphenyl)urocanic Acid Ethyl Ester

Reaction and workup were carried out as in Example 1 using 5.0 g of urocanic acid ethyl ester and 7.6 g of 4-fluorobenzoic acid ethyl ester. Recrystallization of thus obtained crystals from ethyl acetate gave 5.0 g of white crystals, m.p. 173–175° C.

Elemental analyses: for $C_{17}H_{18}N_2O_4$; Calculated (%): C, 64.96; H, 5.77; N, 8.91; Found (%): C, 64.92; H, 5.75; N, 8.87.

EXAMPLE 13

1-((4-Carbomethoymethylphenyl)methyl)urocanic Acid Methyl Ester

Reaction and workup were carried out as in Example 1 using 3.0 g of urocanic acid methyl ester and 4.9 g of 4-bromomethylphenylacetic acid methyl ester. Recrystallization of thus obtained crystals from benzene-isopropyl ether gave 1.0 g of white crystals, m.p. 95–98° C.

Elemental analyses: for $C_{17}H_{18}N_2O_4$; Calculated (%): C, 64.96; H, 5.57; N, 8.91; Found (%): C, 65.18; H, 5.74; N, 8.67.

EXAMPLE 14

1-((2-Methoxyphenyl)piperazinylethyl)urocanic Acid Ethyl Ester

Reaction and workup were carried out as in Example 1 using 1.7 g of urocanic acid ethyl ester and 2.7 g of 4-(2-methoxyphenyl)- 1-chloroethyl-piperazine. Conversion of thus obtained yellow oil to hydrochloric acid salt with 2N hydrochloride acid followed by recrystallization from methanol-acetone gave 3.2 g of white crystal, m.p. 198–200° C. (decomp.).

Elemental analyses: for $C_{21}H_{28}N_4O_3 \cdot 3HCl \cdot 2H_2O$; Calculated (%): C, 47.60; H, 6.65; N, 10.57; Found (%): C, 47.38; H, 6.58; N, 10.56.

EXAMPLE 15

1-(2-(2,4-Dioxo 1,3-dihydroquinazoline-3-yl)ethyl) urocanic Acid Ethyl Ester

Reaction and workup were carried out as in Example 1 using 1.7 g of urocanic acid ethyl ester and 2.3 g of 3-(chloroethyl)-2,4(1H,3H)-quinazolinedione. Recrystallization of thus obtained crystals from dimethylformamide-ethyl acetate gave 1.0 g of white crystals, m.p. 175–178° C.

Elemental analyses: for $C_{18}H_{18}N_2O_4 \cdot 0.75H_2O$; Calculated (%): C, 58.77; H, 5.34; N, 15.23; Found (%): C, 58.69; H, 5.30; N, 15.04.

EXAMPLE 16

1-(Carboethoxymethyl)urocanic Acid Ethyl Ester

Reaction and workup were carried out as in Example 1 using 2.5 g of urocanic acid ethyl ester and 5.0 g of ethyl bromoacetate. Recrystallization of thus obtained crystals from ethyl acetate-hexane gave 1.5 g of pale brown crystals, m.p. 108–110° C.

Elemental analyses: for $C_{12}H_{16}N_2O_4$; Calculated (%): C, 57.13; H, 6.39; N, 11.10; Found (%): C, 56.76; H, 6.32; N, 10.62.

EXAMPLE 17

1-(3-Phenyl-2-propenyl)urocanic Acid Methyl Ester

Reaction and workup were carried out as in Example 1 using 1.5 g of urocanic acid methyl ester and a compound obtained by chlorination of 2.7 g of 3-phenyl-2-propene-1lol with thionyl chloride. Purification of thus obtained crystals by column chromatography (silica gel, elution solvent; ethyl acetate:hexane 1:1) gave 0.9 g of white crystals, m.p. 125–127° C.

Elemental analyses: for $C_{16}H_{16}N_2O_2$; Calculated (%): C, 71.62; H, 6.01; N, 10.44; Found (%): C, 71.40; H, 6.03; N, 10.43.

EXAMPLE 18

Effect of the Present Compound Orally Administered on Rat Type I Allergy

The present compound was assessed for its effect on type I allergy through oral administration.

[Test Compounds]

| | |
|---|---|
| 0.5% Carboxymethyl cellulose sodium solution (CMC-Na) | 5 ml/kg |
| The compound of Example 1 | 100 mg/5 ml/kg |
| The compound of Example 3 | 100 mg/5 ml/kg |
| The compound of Example 6 | 100 mg/5 ml/kg |

[Test Animals]

Male Wistar rats purchased from SLC Japan were used in the test.

[Test Methods]

The rats were intracutaneously injected in the back with 100 µl of antiserum (16-fold dilution) under pentobarbital anesthesia. Forty-eight hrs later, the animals were injected with 5 ml/kg of a mixture of ovalbumin (25 mg/kg) and Evans blue (12.5 mg/kg) to provoke passive anaphylaxis (PCA) reaction.

The rats were sacrificed 30 min after the provocation of PCA reaction and dye-infiltrated region of their back skin was cut out, the dye extracted with 5 ml of formamide and its optical density measured (625 nm).

Each of the test compounds was orally administered 60 min before the provocation of PCA reaction.

[Test Results]

TABLE 1

Effect of the Present Compound on Rat Type I Allergy

| Test compound | Optical density | Inhibition rate (%) |
|---|---|---|
| CMC-Na | 0.578 ± 0.100 | — |
| Compound of Example 1 | 0.413 ± 0.051*[1] | 28.7 |
| Compound of Example 3 | 0.409 ± 0.033*[1] | 29.2 |

The values are mean ± standard deviation (n = 5–6)
Significant difference from CMC-Na: *[1]; $p < 0.01$

TABLE 2

Effect of the Present Compound on Rat Type I Allergy

| Test compound | Optical density | Inhibition rate (%) |
|---|---|---|
| CMC-Na | 0.531 ± 0.076 | — |
| Compound of Example 6 | 0.299 ± 0.031*[3] | 43.6 |

The values are mean ± standard deviation (n = 6)
Significant difference from CMC-Na: *[3]; $p < 0.001$ As evident from Tables 1–2, the present compound significantly suppressed PCA reaction, indicating that it is useful against immediate allergy.

EXAMPLE 19

Effect of the Present Compound Orally Administered or Topically Applied on Type IV Allergy The present compound was assessed for its effect on type IV allergy (efferent phase) through oral and topical administrations, using a DNFB contact-type dermatitis model.

[Test Compounds]
Methanol solutions
the compound of Example 1
the compound of Example 3
the compound of Example 5
the compound of Example 9
the compound of Example 17
the compound of Example 13
the compound of Example 15

[Test Animals]
Male C57BL/6J mice purchased from Clea Japan, Inc. were used.

[Test Methods]
The mice which had their abdominal hair removed on the previous day were sensitized by applying to them on a 1-cm² area of their abdominal surface 25 µl of 0.5% dinitrofluorobenzene (DNFB) dissolved in acetone, under anesthesia with ketamine hydrochloride: xylazine hydrochloride (9:1). Five days after the sensitization procedure, 10 µl of 0.1% DNFB dissolved in acetone was applied to the outer side of their right auricles to induce infammation. Twenty-four hrs after the induction of inflammation, the thickness of the auricles was measured with a dial thickness gauge (manufactured by Ozaki Seisakusho) and the rate of edema calculated by comparing it with pre-induction thickness.

The test compounds were administered either orally or by topically applying 15 µl of its solution onto the outer side of the auricles, 1 hr before the induction.

[Test Results]

The results are shown in Tables 3–5.

TABLE 3

Effect of the Present Compound Topically Applied on Mouse Contact-Type Dermatitis in Auricles

| Test compound | Concentration (%) | Inhibition rate (%) |
|---|---|---|
| Compound of Example 1 | 0.2 | 73.5*[3] |
|  | 0.5 | 83.9*[2] |
| Compound of Example 3 | 0.2 | 47.5*[2] |
|  | 0.5 | 79.2*[3] |
| Compound of Example 5 | 0.2 | 99.9*[3] | n = 9–11
Significant difference from methanol: *[2]; $p < 0.01$, *[3]; $p < 0.001$

TABLE 4

Effect of the Present Compound Topically Applied on Mouse Contact-Type Dermatitis in Auricles

| Test compound | Concentration (%) | Inhibition rate (%) |
|---|---|---|
| CMC-Na | — | — |
| Compound of Example 9 | 0.5 | 89.9*[3] |
| Compound of Example 17 | 0.5 | 70.5*[3] | n = 9–11
Significant difference from CMC-Na: *[3]; $p < 0.001$

TABLE 5

Effect of the Present Compound Orally Administered on Mouse Contact-Type Dermatitis in Auricles

| Test compound | Dose (mg/kg) | Inhibition rate (%) |
|---|---|---|
| CMC-Na | — | — |
| Compound of Example 13 | 30 | 53.8*[2] |
| Compound of Example 15 | 30 | 41.6*[2] | n = 9–11
Significant difference from CMC-Na: *[2]; $p < 0.01$

As evident from Tables 3–5, the present compound either topically or orally administered significantly suppressed the efferent phase in type IV allergy model, indicating that it is useful against delayed allergy.

EXAMPLE 20

Effect of the Present Compound Orally Administered on Type IV Allergy

The present compound was assessed for its effect on type IV allergy (afferent phase) through oral administrations, using a DNFB contact-type dermatitis model.

[Test Compounds]

| | |
|---|---|
| Distilled water | 5 ml/kg |
| The compound of Example 1 | 30 mg/kg |
| The compound of Example 2 | 30 mg/kg |
| The compound of Example 3 | 30 mg/kg |
| The compound of Example 7 | 100 mg/kg |
| The compound of Example 10 | 100 mg/kg |
| The compound of Example 11 | 100 mg/kg |
| The compound of Example 17 | 100 mg/kg |

[Test Animals]

Male C57BL/6J mice purchased from Clea Japan, Inc. were used.

[Test Methods]

The test compounds were orally administered to the mice. One hr later, sensitization was performed by applying 30 μl of 0.5% DNFB acetone solution. Five days after the sensitization procedure, 10 μl of 0.1% DNFB dissolved in acetone was applied to their right auricles to induce contact-type dermatitis. Then, 24 hrs later, the thickness of the auricles was measured and the rate of edema calculated.

[Test Results]

TABLE 6

Effect of the Present Compound on Mouse Contact-Type Dermatitis in Auricles

| Test compound | Inhibition rate (%) |
|---|---|
| Compound of Example 1 | 47.8[*2] |
| Compound of Example 2 | 56.2[*2] |
| Compound of Example 3 | 49.5[*3] |

(n = 7–9)
Significant difference from distilled water: 2; p < 0.01, *[3]; p < 0.001

TABLE 7

Effect of the Present Compound on Mouse Contact-Type Dermatitis in Auricles

| Test compound | Inhibition rate (%) |
|---|---|
| CMC-Na | — |
| Compound of Example 7 | 33.5[*2] |
| Compound of Example 10 | 79.3[*3] |
| Compound of Example 11 | 66.1[*3] |
| Compound of Example 11 | 52.5[*3] | n = 7–9
Significant difference from CMC-Na: 2; p < 0.01, *[3]; p < 0.001

As evident from Tables 6–7, the present compound significantly suppressed the afferent phase in type IV allergy model, indicating that it is useful against delayed type allergy.

EXAMPLE 21

| Oral Tablets | |
|---|---|
| The compound of Example 2 | 30 mg |
| Lactose | 80 mg |
| Potato starch | 17 mg |
| Polyethylene glycol 6000 | 3 mg |

EXAMPLE 22

| Eye drops | |
|---|---|
| The compound of Example 2 (hydrocloride) | 0.3 g |
| Glycerol | 2.5 g |
| Benzalkonium chloride | 0.005 g |
| Sodium acetate | q.s. |
| Sterile purified water | to 100 ml |
| | pH 4.5 |

The above components are mixed and sterilized by filtration to prepare eye drops Industrial Applicability The urocanic acid derivatives of the present invention are soluble in water and can be used advantageously as anti-allergic agents having potent suppressive effect on immediate as well as delayed allergies.

What is claimed is:

1. A urocanic acid derivative represented by the following formula (I) or a pharmacologically acceptable salt thereof (I)

$$\text{structure with imidazole ring bearing CH=CH-C(=O)-OR}_2 \text{ and N-R}_1$$

$$R_1 = -CH_2-CH_2-N\underset{}{\overset{}{\bigcirc}}N-CH(C_6H_5)(2\text{-pyridyl or phenyl})$$

$$-CH_2-CH_2-N\underset{}{\overset{}{\bigcirc}}N-(2\text{-methoxyphenyl})$$

wherein $R_2$ denotes hydrogen or lower alkyl, and Q denotes carbon or nitrogen.

2. The urocanic acid derivative of claim 1 which is 1-(diphenylmethyl-piperazinylethyl)urocanic acid methyl ester or a pharmacologically acceptable salt thereof.

3. The urocanic acid derivative of claim 1 which is 1-(diphenylmethyl-piperazinylethyl)urocanic acid or a pharmacologically acceptable salt thereof.

4. The urocanic acid derivative of claim 1 which is 1-[phenyl(2-pyridyl)methylpiperazinylethyl]urocanic acid methyl ester or a pharmacologically acceptable salt thereof.

5. The urocanic acid derivative of claim 1 which is 1-(diphenyl-methylpiperazinylethyl)urocanic acid ethyl ester or a pharmacologically acceptable salt thereof.

6. The urocanic acid derivative of claim 1 which is 1-((2-methoxyphenyl) piperazinylethyl)urocanic acid ethyl ester or a pharmacologically acceptable salt thereof.

7. A method for preparation of the urocanic acid derivative of claim 1 or a pharmacologically acceptable salt thereof represented by the following scheme:

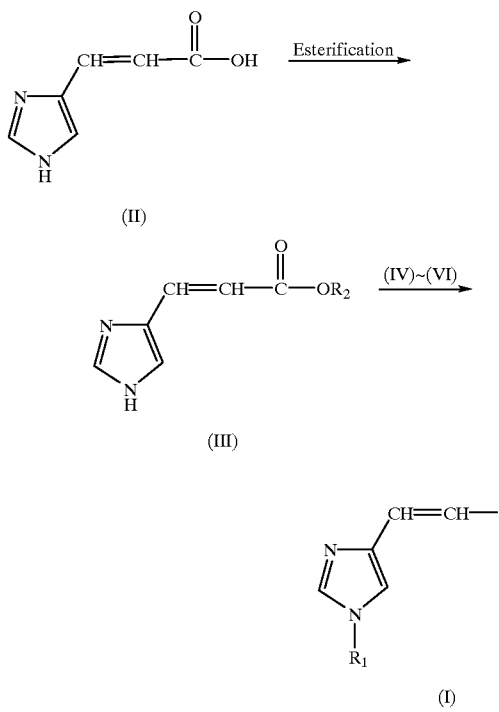

$R_1$ and $R_2$ being defined in claim 1, comprising the steps of:
  a. esteriying urocanic acid (II) to obtain a urocanic acid ester (III); and
  b. reacting the urocanic acid ester (III) with a halogenated compound selected from the group consisting of diphenylmethylpiperazinylethyl chloride (IV), phenyl(2-pyridyl) methylpiperazinylethyl chloride (V), (2-methoxyphenyl)piperazinylethyl chloride (VI) to form a urocanic acid derivative represented by the formula (I),
  c. or, where the urocanic acid derivative to be prepared is a free acid, in which $R_2$ denotes hydrogen, corresponding to the urocanic acid derivative obtained in step b, further hydrolyzing the urocanic acid derivative obtained in step b to form the corresponding fee acid.

8. An antiallergic composition comprising the urocanic acid derivative of one of claims 1 to 4, 5 or 6, or a pharmacologically acceptable salt thereof.

9. A method for treatment of an allergic disease in a patient comprising administering to the patient a therapeutically effective amount of a urocanic acid derivative represented by the following formula (I) or a pharmacologically acceptable salt thereof

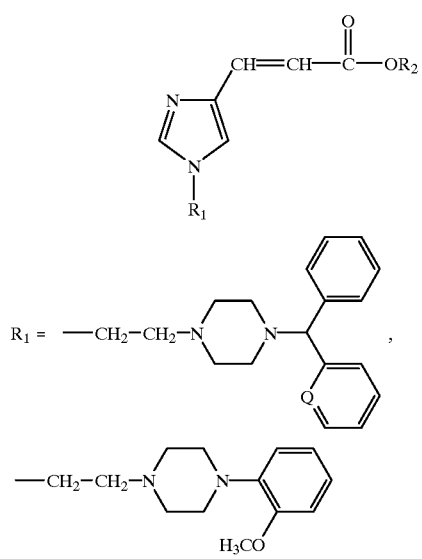

wherein $R_2$ denotes hydrogen or lower alkyl, and Q denotes carbon or nitrogen.

* * * * *